United States Patent [19]

Böhner et al.

[11] 4,000,316

[45] Dec. 28, 1976

[54] INSECTICIDAL AND ACARICIDAL 1-PHENYL-1-P-PROPARGYLOXYPHENYL-2-NITROETHANES

[75] Inventors: Beat Böhner, Binningen; Dag Dawes, Pratteln; Willy Meyer, Basel, all of Switzerland

[73] Assignee: Ciba-Geigy Corporation, Ardsley, N.Y.

[22] Filed: Dec. 29, 1975

[21] Appl. No.: 645,124

Related U.S. Application Data

[62] Division of Ser. No. 437,417, Jan. 28, 1974, Pat. No. 3,950,433.

[30] Foreign Application Priority Data

Feb. 5, 1973 Switzerland ........................ 1620/73
Dec. 14, 1973 Switzerland ...................... 17553/72

[52] U.S. Cl. .................................. 424/340; 424/23; 424/357

[51] Int. Cl.[2] ............................................ A01N 9/24

[58] Field of Search ..................................... 424/340

[56] References Cited

UNITED STATES PATENTS

| | | | |
|---|---|---|---|
| 3,340,308 | 9/1967 | Sterling et al. | 424/340 X |
| 3,840,604 | 10/1974 | Chodnekar et al. | 424/340 X |

*Primary Examiner*—Dale R. Ore
*Attorney, Agent, or Firm*—Frederick H. Rabin

[57] ABSTRACT

1-Phenyl-1-p-propargyloxyphenyl-2-nitro-ethane derivatives of the formula $$X-C_6H_4-CH(Z)-C_6H_4-Y$$

wherein

Z represents the radical $$CH_3-\underset{|}{C}H-NO_2 \text{ or } C_2H_5-\underset{|}{C}H-NO_2,$$

and of the symbols

X and Y one represents hydrogen, fluorine, chlorine, bromine, $C_1$–$C_3$-alkyl, $C_1$–$C_3$-alkoxy, propargyloxy or $C_1$–$C_3$-alkylthio, and the other represents propargyloxy, process for their preparation and their use in pest control.

6 Claims, No Drawings

INSECTICIDAL AND ACARICIDAL 1-PHENYL-1-P-PROPARGYLOXYPHENYL-2-NITROETHANES

This is a division of application Ser. No. 437,417 filed on Jan. 28, 1974 now U.S. Pat. No. 3,950,433.

The present invention relates to 1-phenyl-1-p-propargyloxyphenyl-2-nitroethane derivatives, to processes for their preparation, and to their use in pest control.

The said 1-phenyl-1-p-propargyloxyphenyl-2-nitroethane derivatives have the formula (I)

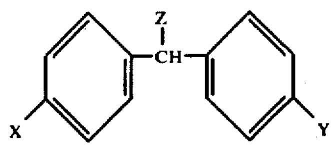

wherein

Z represents the radical $$CH_3-\underset{|}{C}H-NO_2 \text{ or } C_2H_5-\underset{|}{C}H-NO_2,$$

and of the symbols

X and Y one represents hydrogen, fluorine, chlorine, bromine, $C_1$–$C_3$-alkyl, $C_1$–$C_3$-alkoxy, propargyloxy or $C_1$–$C_3$-alkylthio, and the other represents propargyloxy.

The alkyl, alkoxy or alkylthio groups denoted by X or Y can be straight-chain or branched-chain. Such groups are: methyl, methoxy, methylthio, ethyl, ethoxy, ethylthio, n-propyl, n-propoxy, n-propylthio, isopropyl, isopropoxy or isopropylthio.

Compounds of formula I preferred on account of their action are those wherein

Z represents the radical $$CH_3-\underset{|}{C}H-NO_2 \text{ or } C_2H_5-\underset{|}{C}H-NO_2,$$

and of the symbols

X and Y one represents hydrogen, $C_1$–$C_3$-alkyl, $C_1$–$C_3$-alkoxy, propargyloxy or $C_1$–$C_3$-alkylthio, and the other represents propargyloxy.

Particularly preferred, however, are compounds of formula I wherein

Z represents the radical

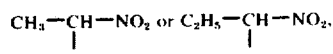

and of the symbols

X and Y one represents hydrogen, $C_1$–$C_3$-alkyl, $C_1$–$C_3$-alkoxy or propargyloxy, and the other represents propargyloxy, and the other represents propargyloxy.

The compounds of formula I can be prepared, e.g. analogously to the following known method:

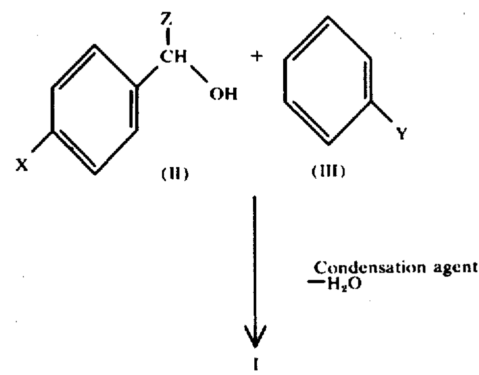

Applicable condensation agents are inorganic acids such as sulphuric acid; organic acids such as acetic acid; Lewic acids such as aluminium chloride or boron trifluoride in the form of complexes with inorganic or organic acids, such as phosphoric acid, acetic acid, etc..

The reaction is performed under normal pressure, at a temperature of between 30° and +100° C, preferably between 0° and 40° C, and optionally in solvents such as, e.g. acetic acid, nitroalkanes or methylene chloride.

The starting materials of formula II are in part known, or can be prepared by methods analogous to known methods, e.g. analogous to those described in the U.S. Pat. No. 2,516,186.

The compounds of formula I have a broad biocidal action, and can be used for the control of various plant and animal pests.

Compared with analogous compounds, the compounds of formula I have a surprisingly better insecticidal action, particularly against *Spodoptera litoralis*, a toxicity level suitable for application and better decomposability.

The action of the compounds according to the invention extends moreover to all development stages, such as eggs, larvae, nymphs, pupae and adults of insects of the families: Aerididae, Blattidae, Gryllidae, Cryllotalpidae, Tettigoniidae, Cimiciade, Phyrrhocoridae, Reduviidae, Aphidiae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Tipulidae, Stomoxydae, Muscidae, Calliphoridae, Culicidae, Trypetidae and Pulicidae, as well as acarids of the families: Ixodidae, Argasidae and Dermanyssidae.

The insecticidal or acaricidal action can be appreciably widened and adapted to suit given circumstances by the addition of other insecticides and/or acaricides. Suitable additives are, e.g. the following active substances:

organic phosphorus compounds, nitrophenols and their derivatives, formamidines, ureas, carbamates and chlorinated hydrocarbons.

The compounds of formula I are combined with particular advantage with substances having a synergistic or intensifying effect. Examples of such compounds are pyrethrin synergists such as piperonly butoxide or Z-(3,4-methylenedioxyphenoxy)-3,6,9-trioxa-undecane (Sesoxane).

The compounds of formula I can be used on their own or together with suitable carriers and/or additives. Suitable carriers and additives may be solid or liquid, and they correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulation of these preparations being effect to a manner commonly known in practice. Also to be mentioned are cattle dips and spray races, in which aqueous preparations are used.

The agents according to the invention are produced in a manner known per se by the intimate mixing and/or grinding of active substances of formula I with suitable carriers, optionally with the addition of dispersing agents or solvents which are inert to the active substances. The active substances can be obtained and used in the following forms:

solid preparations:

dusts, scattering agents, granulates coated granulates, impregnated granulates and homogeneous granulates;

liquid preparations:

a. water dispersible active-substance concentrates: wettable powders, pastes, emulsions;

b. solutions.

The content of active substance in the described agents is between 0.1 and 95%; it is to be mentioned in this connection that in the case of application from an aeroplane, or by means of other suitable devices, concentrations of up to 99.5% can be employed, or even the pure active substance.

The active substances of formula I can be prepared, for example, as follows:

Dusts:

The following substances are used in the preparation of (a) a 5% dust, and (b) a 2% dust:

a. 5 parts of active substance,
95 parts of talcum;

b.
2 parts of active substance,
1 part of highly dispersed silicic acid,
97 parts of talcum The active substances are mixed and ground with the carriers.

Granulate:

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3 – 0.8 mm).

The active substance is mixed with epichlorhydrin and dissolved with 6 parts of acetone; the polyethylene glycol and cetyl polyglycol ether are then added. The solution thus obtained is sprayed on to kaolin, and the acetone subsequently evaporated off in vacuo.

Wettable powder:

The following constituents are used for the preparation of (a) a 40%, and (b) and (c) a 25%, and (d) a 10% wettable powder:

a.
40 parts of active substance,
5 parts of sodium lignin suplhonate,
1 part of sodium dibutyl-naphthalene sulphonate,
54 parts of silici acid.

b.
25 parts of active substance.
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silici acid,
19.5 parts of Champagne chalk,
28.1 parts of kaolin.

c.
25 parts of active substance,
2.5 parts of isooctylphenoxy-polyoxyethylene-ethane
1.7 parts of Champagne chalk/hydroxethyl cellulose mixture (1:1),
8.3 parts sodium aluminium silicate,
16.3 parts of kieselguhr,
46 parts of Kaolin d.
10 parts of active substance,
3 parts of a mixture of the sodium salts of saturated fatty alcohol sulphates,
5 parts of naphthalenesulphonic acid/formaldehyde, condensate.
82 parts of kaoline.

The active substances are intimately mixed, in suitable mixers, with the additives, the mixture being then ground in the appropriate mills and rollers. Wettable powders are powders are obtained which can be diluted with water to give suspensions of any desired concentration.

Emulsifiable concentrates:

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkylaryl-sulphonate calcium salt.
40 parts of dimethylformamide,
43.2 parts of xylene.

b.
25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsions of any desired concentration.

Spray:

The following constituents are used to prepare a 5% spray:

5 parts of active substance,
1 part of epichlorhydrin,
94 parts of ligroin (boiling limits 160°–190° C).

EXAMPLE 1

Preparation of 1-p-ethoxyphenyl-1-p-propargyl-oxyphenyl-2-nitropropane 45 g of 1-p-ethoxyphenyl-2-nitro-1-propanol and 26.4 g of phenylpropargyl ether are dissolved in 80 ml of methylene chloride, and the solution added dropwise at 0° C, with vigorous stirring, to 180 g of conc. $H_2SO_4$ and 20 ml of water. After completion of the addition, stirring is continued for a further hour at room temperature. the reaction mixture is poured on 400 ml of ice water, and twice extracted with 250 ml of methylene chloride each time. After drying over $Na_2SO_4$, the solvent is evaporated off in vacuo, and the crude product dried in high vacuum to obtain 60 g of yellow oil (still contains some carbinol). The crude product can be purified by chromatography on silica gel with petroleum ether containing 5% of ethyl acetate to thus yield 47 g of pure product in the form of a light-yellow oil having a refractive index of $n_D^{20} = 1.5654$.

The following compounds are prepared in an analogous manner:

R, $NO_2$ — CH — CH — (two phenyl rings); $CH \equiv C—CH_2O$ on one ring, Y on the other

| Y | R = $—CH_3$ | R = $—C_2H_5$ |
|---|---|---|
| $—C_3H_7(i)$ | $n_D^{22°} = 1,5565$ | $n_D^{20°} = 1,5491$ |
| $—OCH_3$ | $n_D^{20°} = 1,5763$ | $n_D^{20°} = 1,5621$ |
| $—OC_2H_5$ | $n_D^{40°} = 1,5654$ | $n_D^{22°} = 1,5570$ |
| H | | $n_D^{20°} = 1,5632$ |
| $—CH_3$ | $n_D^{20°} = 1,5637$ | M.P. 126–127° C |
| $—C_2H_5$ | $n_D^{20°} = 1,5576$ | $n_D^{20°} = 1,5541$ |
| F | | M.P. 89–90° C |
| Cl | | $n_D^{20°} = 1,5665$ |
| $—OC_3H_7(n)$ | $n_D^{20°} = 1,5552$ | M.P. 91–92° C |
| $—OC_3H_7(i)$ | $n_D^{20°} = 1,5588$ | M.P. 109–111° C |
| $—OCH_2—C \equiv CH$ | $n_D^{20°} = 1,5677$ | $n_D^{20°} = 1,5619$ |
| $—SCH_3$ | $n_D^{20°} = 1,5923$ | $n_D^{20°} = 1,5975$ |
| $—SC_2H_5$ | $n_D^{20°} = 1,5844$ | $n_D^{20°} = 1,5937$ |
| $—SC_3H_7(n)$ | $n_D^{20°} = 1,5850$ | $n_D^{20°} = 1,5808$ |
| $—SC_3H_7(i)$ | $n_D^{20°} = 1,5834$ | $n_D^{20°} = 1,5722$ |

EXAMPLE 2

A. Insecticidal stomach poison action

Cotton and potato plants were sprayed with a 0.05% aqueous active-substance emulsion (obtained from a 10% emulsifiable concentrate).

After the drying of the resulting coating, *Spodoptera litoralis* or *Heliothis virescens* larvae $L_3$ were placed on the cotton plants, and Colorada beetle larvae (*Leptinotarsa decemlineata*) on the potato plants. The test was carried out at 24° C with 60% relative humidity.

The compounds according to Example 1 exhibited in the above test a good insecticidal stomach poison action against *Spodoptera litoralis*, *Heliothis virescens* and *Leptinotarsa decemlineata* larvae.

B. Contact action against stored-food pests and house pests

Five parts by weight of an active substance and five parts by weight of talcum are mixed together and finely ground. A further 90 parts of weight of talcum are mixed in to obtain a 5% dust; this can be used as a starting mixture for 1:1-dilutions for graduated tests of the active substances with respect to their action against stored-food pests and house pests.

The test insects,

German cockroach (*Phyllodromia germanica*)
American cockroach (*Periplaneta americana*)
Russian cockroach (*Blatta orientalis*),
yellow mealworm imago (*Tenebrio molitor*) larvae,
larder beetle imago (*Dermestes frischii*) larvae,
pelt beetle larvae (*Attagenus pellio*),
European house cricket (*Acheta domesticus*), and
grain weevil (*Sitophilus granarius*), are placed on filter paper in glass dishes, the filter paper having been treated with 2 g of the 5% formulation. The amount of active substance is 100 mg of AS/m². The applied 1:1-dilutions then give 2.5%, 1.25%,, 0.6%, 0.31% and 0.16% active-substance formulations, which correspond to active-substance amounts of 50, 25, 12.5, 6.2 and 3.1 mg of AS/m² when 2 g of the respective dust formulation is used for each glass dish.

Compounds according to Example 1 exhibited in the above test contact action against *Phyllodromia germanica*, *Periplaneta americana*, *Blatta orientalis*, *Tenebrio molitor*, *Dermestes frischii*, *Attagenus pellio*, *Acheta domesticus* and *Sitophilus granarius*.

C. Contact action against adults of *Aedes aegypti*

With use of an acetone solution, amounts of 1, 0.1, 0.01 and 0.001 mg of active substance per Petri dish were applied. Each test was performed twice with 10 mosquitoes for each concentration. Both the rate of action and the applied amount for a 100% mortality were taken into account in effecting an evaluation.

Compounds according to Example 1 exhibited in the above test a favourable action against adults of *Aedes aegypti*.

EXAMPLE 3

Action against *Chilo suppressalis*

Rice plants of the variety Caloro were planted, 6 plants per pot, in plastic pots having a top diameter of 17 cm, and grown to a height of ca. 60 cm. Infestation with *Chilo suppressalis* larvae ($L_1$; 3–4 mm long) was carried out 2 days after application of the active substance in granular form (amount applied = 8 kg of active substance per hectare) to the paddy water. The evaluation of the insecticidal action was made 10 days after application of the granules.

Compounds according to EXAMPLE 1 were effective against *Chilo suppressalis* in the above test.

EXAMPLE 4

Action against ticks

A *Rhipicephalus bursa*

In each case, five adult ticks or 50 tick larvae were placed into a small glass tube; the test tubes were then immersed for 1 to 2 minutes in 2 ml of an aqueous emulsion from a diluted series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae for 2 days. were two repeats for each test.

B. *Amblyomma hebraeum*

With a solution series analogous to that in Test A, tests were carried out using in each case 20 larvae.

Compounds according to Example 1 were effective in these tests against adults and larvae of *Rhipicephalus bursa* and against larvae of *Amblyomma hebraeum*.

What we claim is:

1. An insecticidal and acaricidal composition comprising (1) an insecticidally or acaricidally effective amount of a compound selected from the group consisting of 1-p-ethoxyphenyl-1-1-p-propargyloxyphenyl-2-nitropropane, 1-p-isopropylphenyl-1-p-propargyloxyphenyl-2-nitropropane, 1-p-isopropylphenyl-1-p-propargyloxyphenyl-2-nitrobutane, 1-p-ethylphenyl-1-p-propargyloxyphenyl-2-nitropropane and 1-p-ethylphenyl-1-p-propargyloxyphenyl-2-nitrobutane, and (2) an inert carrier therefor.

2. A method for combatting insects and acarids which comprises applying thereto an insecticidally or acaricidally effective amount of 1-p-ethoxyphenyl-1-p-propargyloxyphenyl-2-nitropropane.

3. A method for combatting insects and acarids which comprises applying thereto an insecticidally or acaricidally effective amount of 1-p-isopropylphenyl-1-p-propargyloxyphenyl-2-nitropropane.

4. A method for combatting insects an acarids which comprises applying thereto an insecticidally or acaricidally effective amount of 1-p-isopropylphenyl-1-p-propargyloxyphenyl-2-nitrobutane.

5. A method for combatting insects and acarids which comprises applying thereto an insecticidally or acaricidally effective amount of 1-p-ethylphenyl-1-p-propargyloxyphenyl-2-nitropropane.

6. A method for combatting insects and acarids which comprises applying thereto an insecticidally or acaricidally effective amount of 1-p-ethylphenyl-1-p-proparguloxyphenyl-2-nitrobutane.

* * * * *

UNITED STATES PATENT AND TRADEMARK OFFICE

CERTIFICATE OF CORRECTION

PATENT NO. : 4,000,316

DATED : December 28, 1976

INVENTOR(S) : Beat Böhner et al.

It is certified that error appears in the above-identified patent and that said Letters Patent are hereby corrected as shown below:

IN THE CLAIMS:

Claim 1, line 19 should read as follows:

"sisting of 1-p-ethoxyphenyl-1-p-propargyloxyphenyl"

Claim 6, line 22 should read as follows:

"propargyloxyphenyl-2-nitrobutane"

Signed and Sealed this

Fifth Day of April 1977

[SEAL]

*Attest:*

RUTH C. MASON
*Attesting Officer*

C. MARSHALL DANN
*Commissioner of Patents and Trademarks*